United States Patent
Itonaga et al.

(10) Patent No.: US 6,527,727 B2
(45) Date of Patent: Mar. 4, 2003

(54) SPHYGMOMANOMETER CUFF CAPABLE OF BLOCKING BLOOD FLOW FAVORABLY EVEN WITH SMALL WIDTH IN WRAPPING DIRECTION

(75) Inventors: Kazunobu Itonaga, Kyoto (JP); Takahide Tanaka, Kyoto (JP); Yoshihiko Sano, Kyoto (JP); Hiroyuki Kato, Kyoto (JP); Hironori Sato, Kyoto (JP)

(73) Assignee: Omron Corporation, Kyoto (JP)

( * ) Notice: Subject to any disclaimer, the term of this patent is extended or adjusted under 35 U.S.C. 154(b) by 0 days.

(21) Appl. No.: 09/781,977

(22) Filed: Feb. 14, 2001

(65) Prior Publication Data

US 2001/0016692 A1 Aug. 23, 2001

(30) Foreign Application Priority Data

Feb. 17, 2000 (JP) .................................. 2000-039036

(51) Int. Cl.⁷ .................................................. A61B 5/02
(52) U.S. Cl. ........................ 600/499; 600/490; 606/202
(58) Field of Search ........................... 600/499; 606/202

(56) References Cited

U.S. PATENT DOCUMENTS

| 2,826,191 | A | * | 3/1958 | Burns ......................... 600/499 |
| 3,279,459 | A | * | 10/1966 | Schenker ................... 600/499 |
| 5,511,551 | A | * | 4/1996 | Sano et al. ................. 600/499 |
| 5,741,295 | A | * | 4/1998 | McEwen .................... 606/202 |
| 6,336,901 | B1 | * | 1/2002 | Itonaga et al. ............. 600/499 |

FOREIGN PATENT DOCUMENTS

JP          2840075         10/1998

* cited by examiner

Primary Examiner—Max Hindenburg
Assistant Examiner—Patricia C. Mallari
(74) Attorney, Agent, or Firm—Morrison & Foerster LLP

(57) ABSTRACT

A bladder incorporated in a cuff includes an outer wall located at the outer side, an inner wall located at the inner side, side walls connected to both side ends of the outer wall and the inner wall in the wrapping direction, and folded inward of the bladder, and a joint connecting the side walls inside the bladder. A sphygmomanometer cuff is provided that can maintain the former configuration even when inflated or deflated without change in the width even if the bladder is inflated, and that does not dilate in the width direction when inflated.

8 Claims, 6 Drawing Sheets

SPHYGMOMANOMETER CUFF CAPABLE OF BLOCKING BLOOD FLOW FAVORABLY EVEN WITH SMALL WIDTH IN WRAPPING DIRECTION

BACKGROUND OF THE INVENTION

1. Field of the Invention

The present invention relates to a cuff for a sphygmomanometer, particularly to a sphygmomanometer cuff wrapped around the region of measurement such as the upper arm or wrist used to increase the pressure at that region to measure blood pressure.

2. Description of the Background Art

FIG. 6 is a perspective view of an entire sphygmomanometer cuff. Referring to FIG. 6, a sphygmomanometer cuff 70 includes an outer cuff piece 71, an inner cuff piece 72, a bladder 73 provided inside a band-like bladder formed of outer cuff piece 71 and inner cuff piece 72, and a clip plate 74 arranged outside bladder 73 to suppress the outward swell of bladder 73 and maintain a predetermined curved configuration in an elastic manner. Hook-and-loop fasteners 75 and 76 are provided at outer cuff piece 71 and inner cuff piece 72, respectively. Cuff 70 is fastened to the measurement region in a wrapped-around manner by hook-and-loop fasteners 75 and 76.

Such a cuff 70 is provided in a wrist sphygmomanometer as shown in FIG. 7, for example, and attached to a sphygmomanometer unit 80.

Bladder 73 used in the aforementioned cuff 70 includes an outer wall 61 and an inner wall 62, as shown in FIG. 4 (the upper portion corresponds to a deflated state and the lower portion corresponds to an inflated state). Walls 61 and 62 are fixed with each other by melting or the like at both ends 63 in the wrapping direction.

Inflation of bladder 73 results in a smaller width of bladder 73 (the dimension perpendicular to the wrapping direction). Pressure caused by inflation of bladder 73 may not be applied sufficiently to the artery located in the measurement region around which cuff 70 is wrapped to degrade the reliability of the blood pressure measurement precision. Particularly in the case of cuffs for wrist sphygmomanometers, there are many disadvantages in blocking the flow of blood since there are more tendons and the like at the wrist than at the upper arm. Therefore, the cuff for a wrist sphygmomanometer requires a higher performance of blocking blood flow than that of the cuff for the upper arm. It is difficult to apply sufficient pressure to the region where blood flow is to be blocked and the blood flow could not be blocked favorably if the conventional cuff configuration was used in which the width becomes smaller.

Japanese Patent No. 2840075 B2 discloses a cuff band for a wrist sphygmomanometer as schematically shown in FIG. 5 (the upper portion corresponds to a deflated state and the lower portion corresponds to an inflated state). Referring to FIG. 5, a blood blocking cuff (bladder) 50 is formed in a bladder configuration with two inner and outer cuff pieces 51 and 52 and side walls 53. Side wall 53 serving to inflate blood blocking cuff 50 in the thickness direction by the introduction of air into blood blocking cuff 50 is provided in a direction (the direction indicated by the arrow in FIG. 5) crossing the direction of inner cuff piece 52 wrapping around the wrist.

Since side walls 53 project outwards when air is introduced into blood blocking cuff 50, the width of blood blocking cuff 50 does not change although it is inflated. However, there is a problem that, after air is discharged, side walls 53 will not return to the original configuration of inward folded state.

SUMMARY OF THE INVENTION

In view of the foregoing, an object of the present invention is to provide a sphygmomanometer cuff that can maintain its former configuration in both the inflated and deflated state without change in the width even if the bladder is inflated and without expanding in the width direction when inflated.

To achieve the above object, the sphygmomanometer cuff of the present invention includes a bladder that inflates and deflates by the input and output of a fluid. The bladder includes an outer wall located at the outer side, an inner wall located at the inner side, a side wall connected to both ends in the wrapping direction of respective outer and inner walls, and folded inward in the bladder, and a joint coupling the side walls inside the bladder.

Since the bladder includes a joint that couples both side walls within the bladder in addition to the outer wall, inner wall and side walls in this cuff, the bladder maintains its configuration in which both side walls are folded when there is no fluid (water, air, or the like) in the bladder. Introduction of a fluid into the bladder causes the side walls to dilate outward from the folded state. However, since side walls are connected by the joint, the side walls do not project outwards, and the cuff is inflated in the direction of the thickness as the side walls extend substantially straight in the direction of the thickness of the cuff. Therefore, the bladder does not expand in the direction of the width when inflated. The width of the bladder hardly differs from that prior to inflation. When the fluid in the bladder is discharged, the side walls easily return to the folded state by virtue of the joint as the outer wall and the inner wall approximate each other and is eventually restored to the state prior to inflation.

By setting the side walls harder than the outer and inner walls in the above structure, the balance of weight of the bladder is improved particularly during inflation, so that pressure can be applied more stably at the measurement region with the cuff.

The details of setting both side walls harder than the outer wall and the inner wall will be described here. In the case where the side wall, the outer wall, and the inner wall are all to be formed of the same material, for example using a soft vinyl chloride sheet of the same type, the thickness of the side wall is set to 0.4 mm and the thickness of the outer wall and the inner wall is set to 0.2 mm, by way of example. Alternatively, when different materials are to be used, the type and thickness of each material is to be selected appropriately so that the side wall is harder than the outer wall and the inner wall.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Embodiments of the present invention will be described hereinafter with reference to the drawings.

Figure 1:
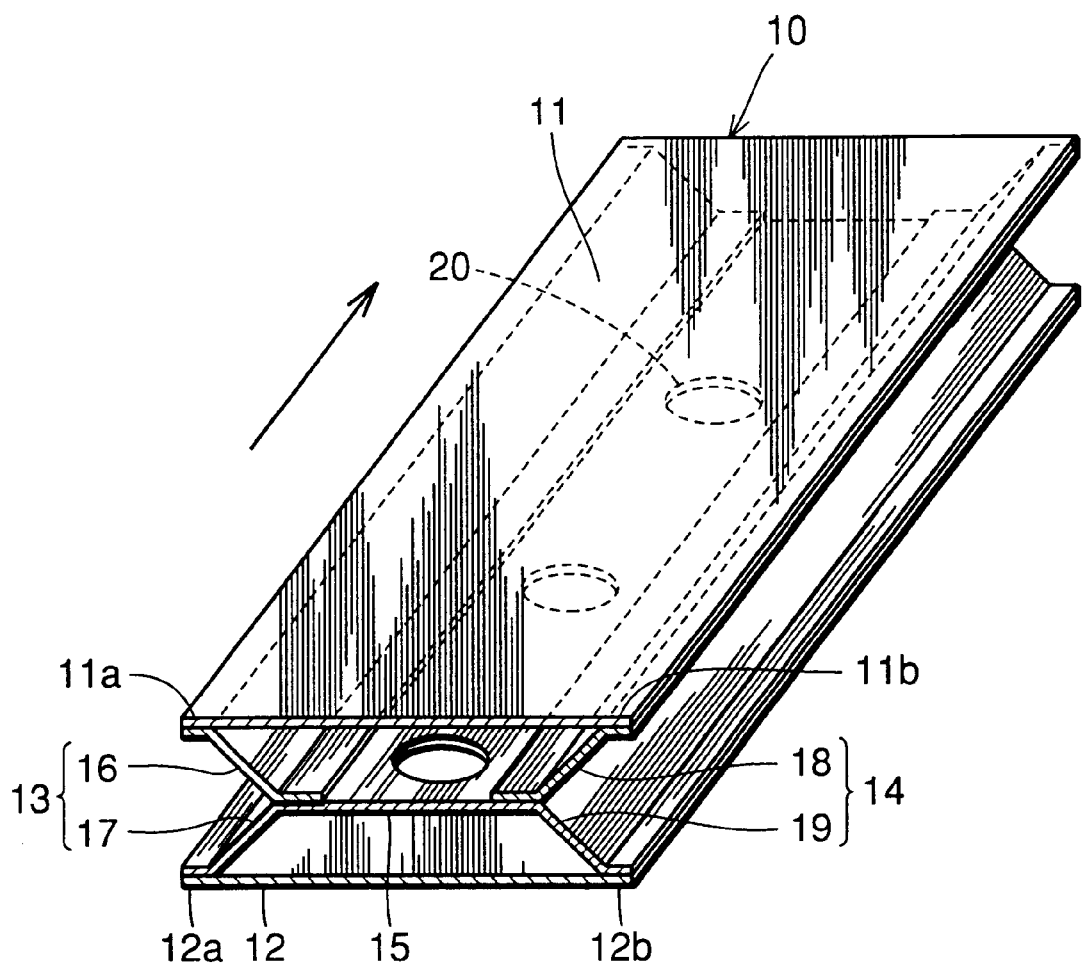
FIG. 1 is a perspective view of the portion of the bladder incorporated in a sphygmomanometer cuff according to an embodiment of the present invention.

Referring to FIG. 1, a bladder 10 incorporated in a sphygmomanometer cuff includes an outer wall 11 located at the outer side, an inner wall 12 located at the inner side, side walls 13 and 14 connected to respective side ends 11a and 11b, 12a and 12b in a direction crossing the wrapping direction of outer and inner walls 11 and 12 (the direction indicated by the arrow in FIG. 1), and folded inward of bladder 10, and a joint 15 coupling side walls 13 and 14 inside bladder 10. Side wall 13 is fixed to side ends 11a and 12a of outer and inner walls 11 and 12 by an adhesive, by melting or the like. Similarly, side wall 14 is fixed to side ends 11b and 12b of outer and inner walls 11 and 12 by an adhesive, by melting or the like.

In bladder 10, side wall 13 is formed of pieces 16 and 17. Piece 17 is provided integrally with joint 15. Piece 16 is fixed at the border between joint 15 and piece 17 by an adhesive, by melting or the like. Similarly, side wall 14 is formed of pieces 18 and 19. Piece 19 is provided integrally with joint 15. Piece 18 is fixed at the border between joint 15 and piece 19.

Bladder 10 has holes 20 provided at an appropriate interval in joint 15. This hole 20 provides communication between the chambers in bladder 10 partitioned into two by joint 15. Air communication is improved by the formation of hole 20.

When air is delivered into bladder 10 of above-described structure, outer wall 11 and inner wall 12 inflate in the direction of thickness of bladder 10 by air pressure, whereby side walls 13 and 14 extend in the direction of thickness. However, side walls 13 and 14 extend to substantially an upright status at most without projecting outwards since side walls 13 and 14 are connected by joint 15. Therefore, bladder 10 does not expand in the direction of the width during inflation. The width of bladder 10 hardly differs from that prior to inflation. When air is discharged from bladder 10, side walls 13 and 14 easily return to the folded state by joint 15 as outer wall 11 and inner wall 12 come closer to each other to be eventually restored to the status prior to inflation.

Figure 2:
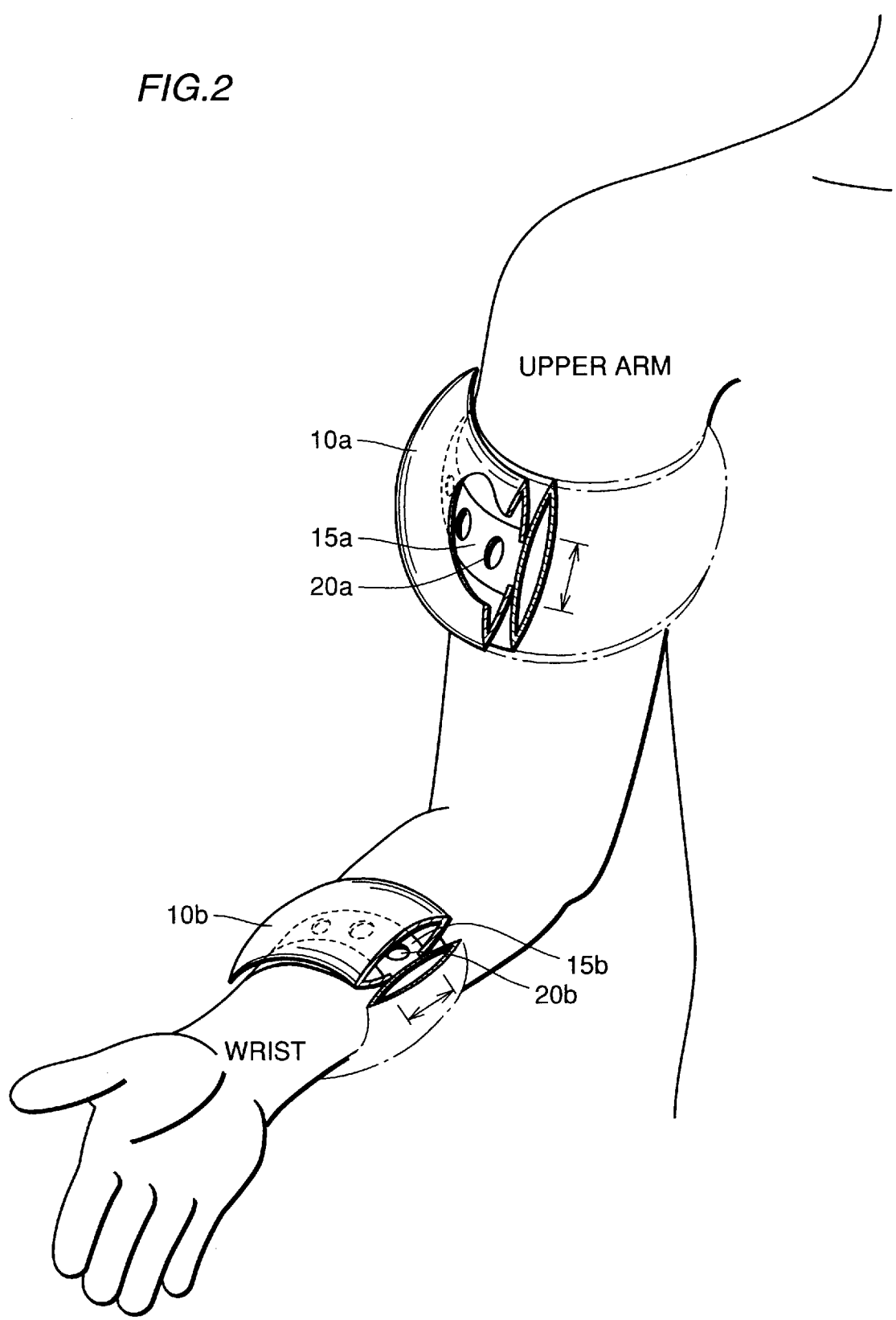
FIG. 2 is a partial sectional view of the bladder incorporated in a sphygmomanometer cuff attached to the upper arm and the wrist.

FIG. 2 is a partial sectional view of the bladder when the sphygmomanometer cuff with the bladder of FIG. 1 is wrapped around the upper arm and the wrist. Referring to the upper portion in FIG. 2, bladder 10a will apply pressure flatly around the arm at the upper arm portion indicated by the arrow in FIG. 2 by virtue of joint 15a and hole 20a.

Referring to the lower portion of FIG. 2 where the cuff is wrapped around the wrist, bladder 10b applies pressure flatly around the wrist at the portion indicated by the arrow in FIG. 2 by virtue of joint 15b and hole 20b.

As a result, sufficient pressure can be applied at the region of interest to block the flow of blood favorably.

In this bladder 10, the balance of weight of bladder 10 during the inflation status can be improved by setting side walls 13 and 14 harder than outer wall 11 and inner wall 12. Pressure can be applied more stably at the measurement region using the cuff with bladder 10.

Figure 3:
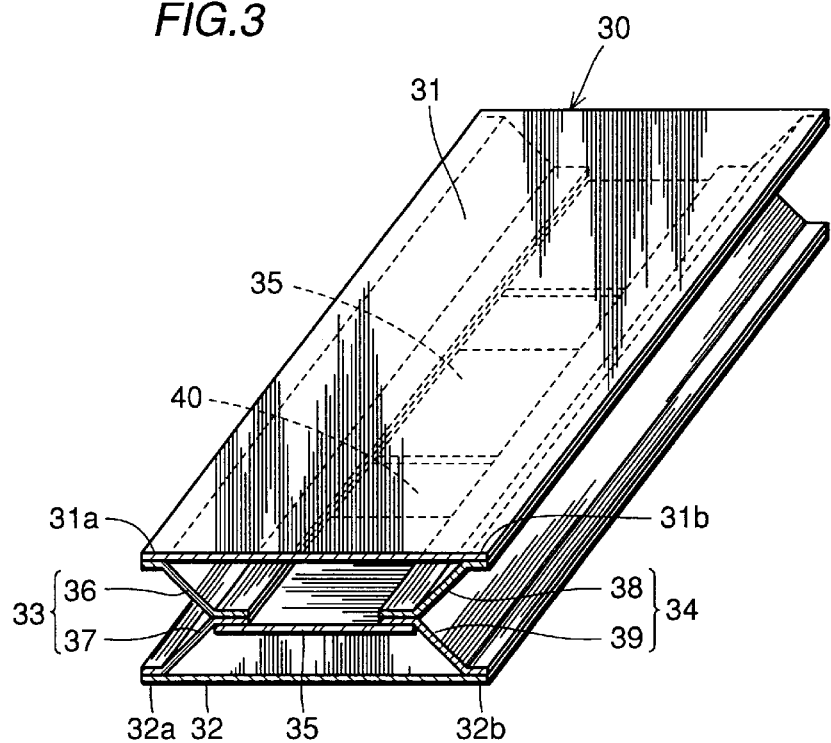
FIG. 3 is a perspective view of the portion of a bladder incorporated in a sphygmomanometer cuff according to another embodiment of the present invention.
Figure 4:
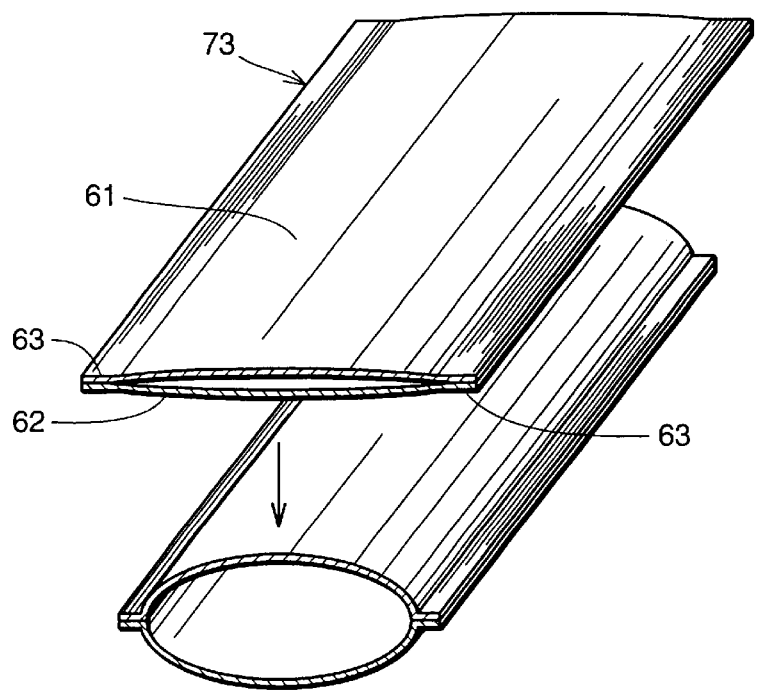
FIG. 4 is a partial perspective view of a conventional bladder corresponding to a deflated status (upper portion) and an inflated state (lower portion).
Figure 5:
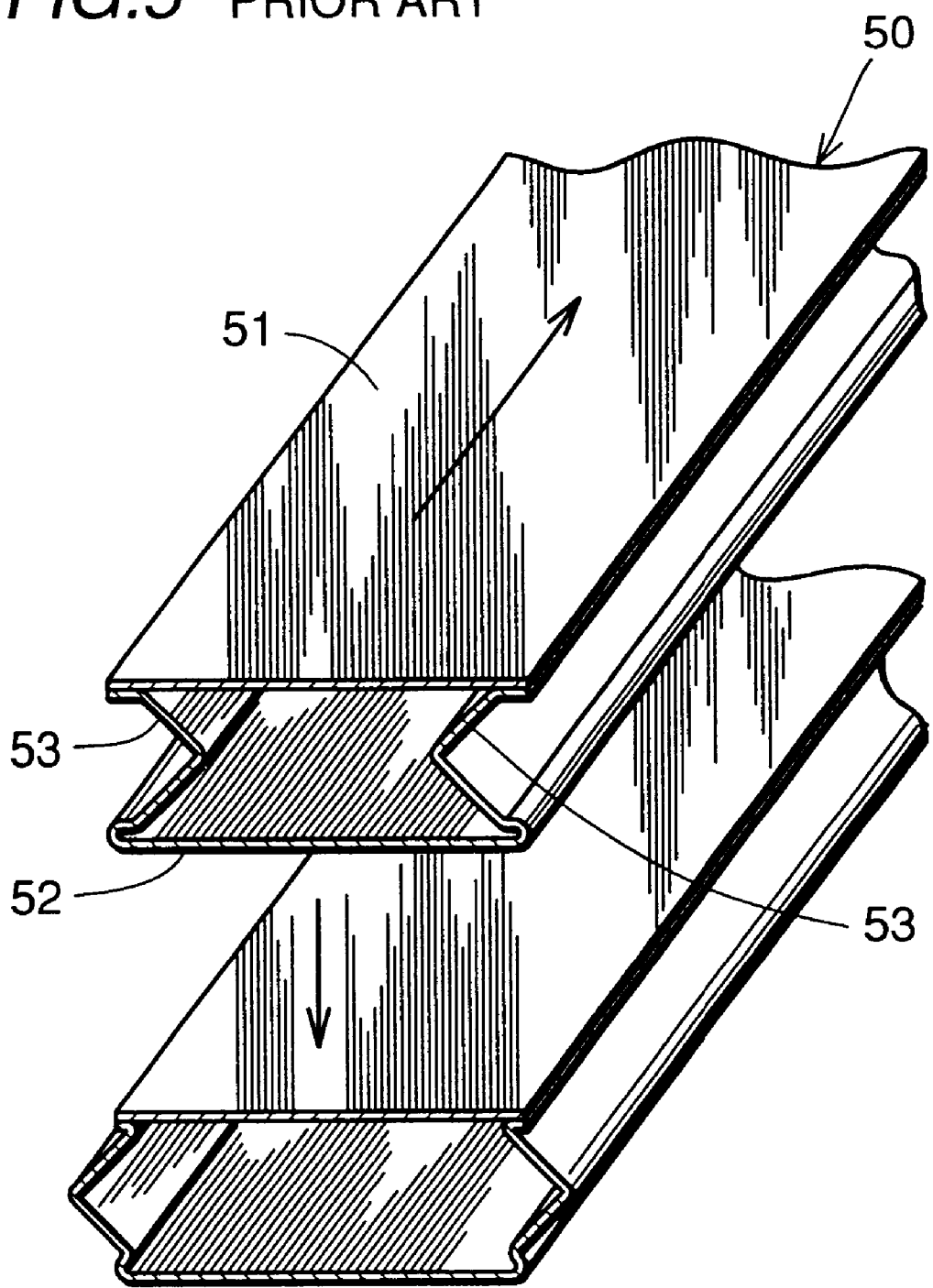
FIG. 5 is a partial perspective view of another conventional bladder corresponding to a deflated status (upper portion) and an inflated status (lower portion).
Figure 6:
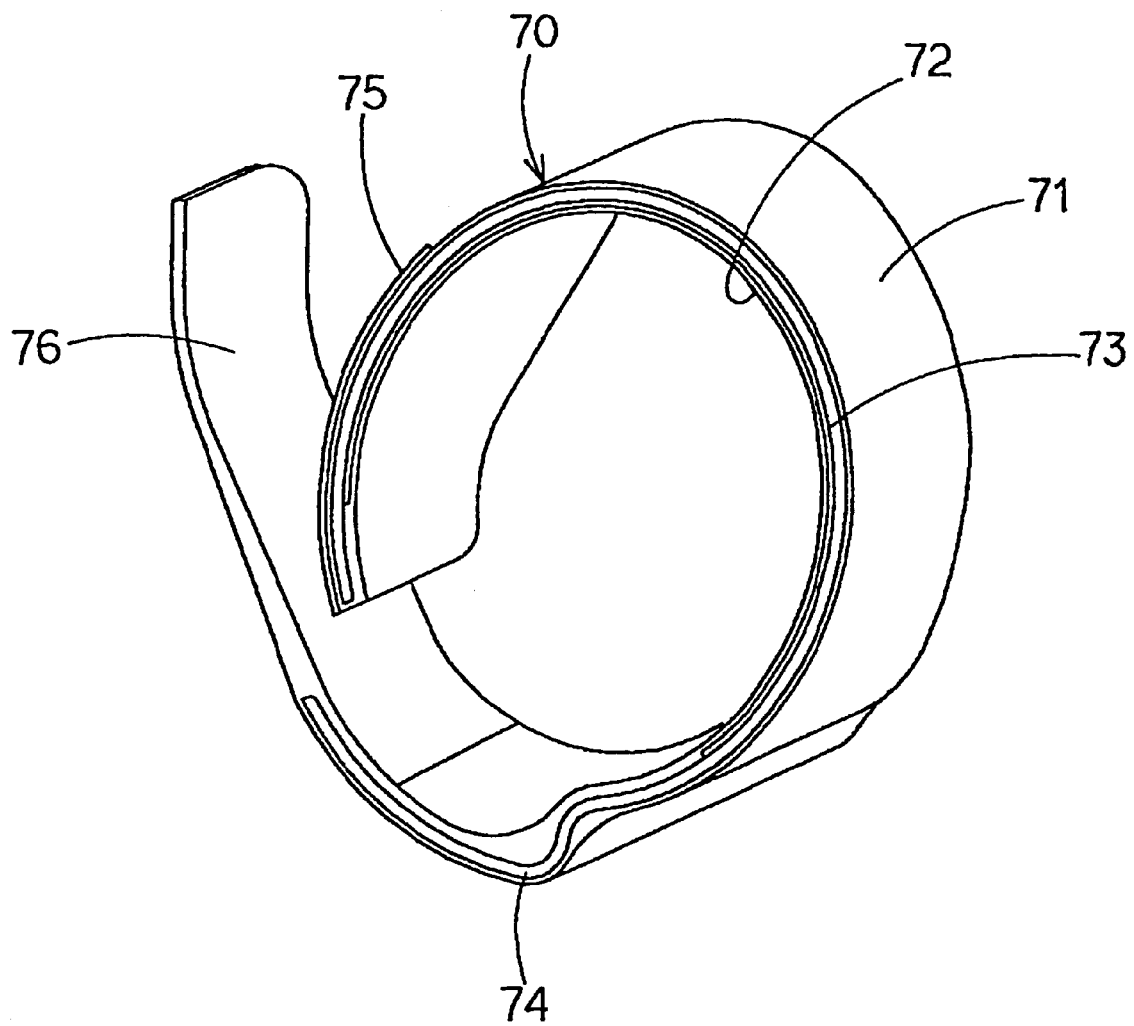
FIG. 6 is a perspective view showing an example of a general bladder.
Figure 7:
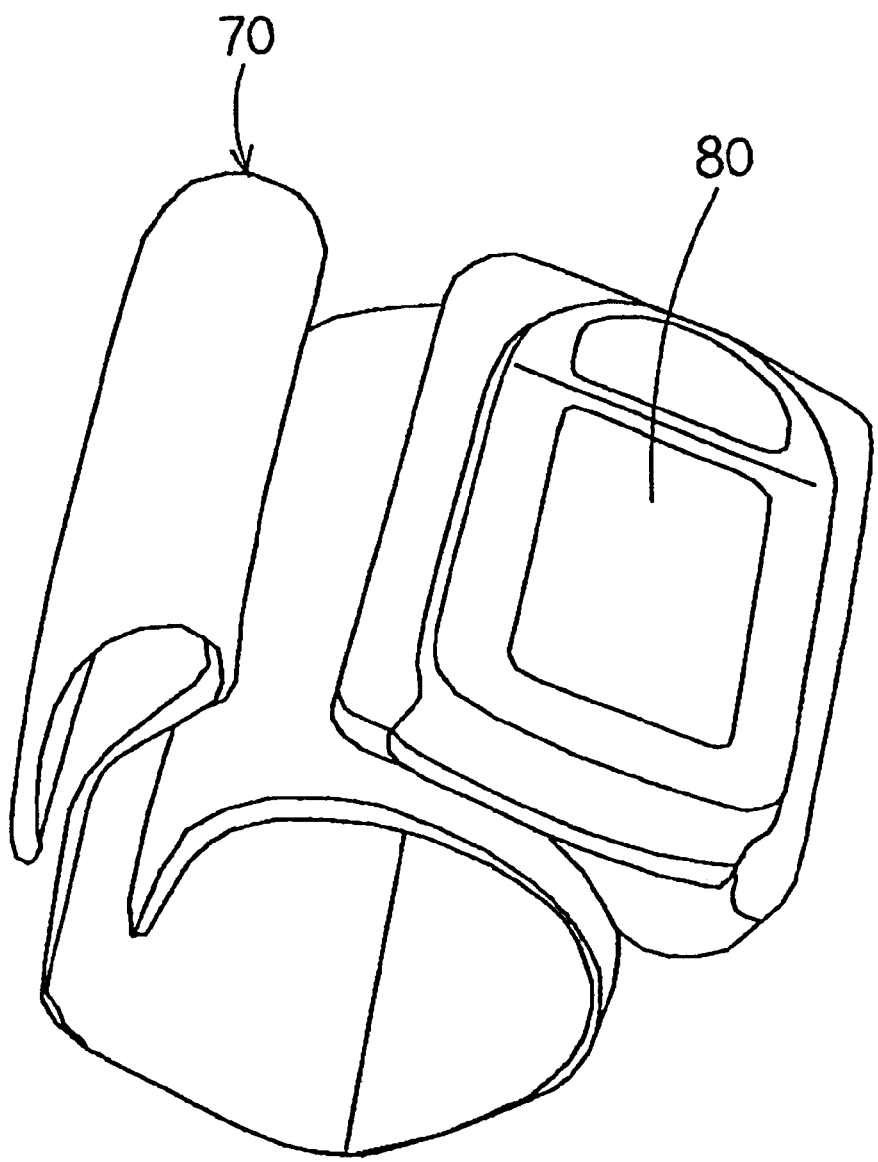
FIG. 7 is a perspective view of a wrist sphygmomanometer with a bladder such as that of FIG. 6.

FIG. 3 is a partial perspective view of a bladder incorporated in a sphygmomanometer cuff according to another embodiment of the present invention.

Referring to FIG. 3, this bladder 30 includes an outer wall 31, an inner wall 32, side walls 33 and 34, and a joint 35. Side wall 33 is formed of pieces 36 and 37. Pieces 36 and 37 are fixed integrally, and fastened to the end of joint 35. Similarly, side wall 34 is formed of pieces 38 and 39. Pieces 38 and 39 are fixed integrally, and fastened to the end of joint 35.

Joint 35 of the present embodiment does not form a band as joint 15 of bladder 10 of the previous embodiment. A plurality of joints 35 (three joints in this embodiment) are fixed to side walls 33 and 34 at appropriate intervals, whereby side walls 33 and 34 are connected by joints 35. Hole 40 formed between joints 35 functions as an air channel (communication). Bladder 30 of the present embodiment provides advantageous effects similar to those of bladder 10.

Although the shape of the hole is preferably circular, a hole in the shape of a polygon can also be used provided that a curved portion is formed so that stress is not concentrated at the corner.

Instead of forming a hole in joint 15, joint 15 having a mesh configuration all over can be employed.

In the above embodiments, the outer wall, the inner wall, and the side walls are produced individually and then fastened. Alternatively, a bladder having the outer wall, the inner wall, the side walls, and the joint formed integrally by injection molding can be used.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A sphygmomanometer cuff including a bladder that inflates and deflates by input and output of a fluid and is adapted to wrap around a region of a person along a predetermined wrapping direction, the bladder comprising:
an outer wall located at an outer side,
an inner wall located at an inner side opposite the outer wall,
a pair of side walls connected to side ends of the outer wall and the inner wall in a direction crossing the wrapping direction, and folded inward of the bladder, and
a joint connecting the pair of side walls inside the bladder.

2. The sphygmomanometer cuff according to claim 1, wherein said side walls are harder than the outer wall and the inner wall.

3. The sphygmomanometer cuff according to claim 1, wherein a hole is provided in said joint.

4. The sphygmomanometer cuff according to claim 3, wherein a plurality of said holes are provided.

5. The sphygmomanometer cuff according to claim 3, wherein said hole is a round hole.

6. The sphygmomanometer cuff according to claim 1, wherein said bladder is formed integrally.

7. A sphygmomanometer cuff including a bladder that inflates or deflates by introducing or discharging fluid into or from the bladder, said bladder comprising:

a first plane adapted to abut against a wrist or an arm, and extending in a first direction which is a circumferential direction thereof, a second plane opposite the first plane, wherein the first and second planes have a first dimension in a second direction crossing the first direction, third and fourth planes opposite each other to connect the first and second planes mutually at an end portion in the second direction, and a connection member connecting the third and fourth planes at respective middle portions at a second dimension shorter than the first dimension.

8. The sphygmomanometer cuff according to claim 7, wherein a hole is formed in the connection member.

* * * * *